United States Patent
Sato et al.

(10) Patent No.: US 10,323,264 B2
(45) Date of Patent: Jun. 18, 2019

(54) METHOD FOR PRODUCING METHACRYLYL-COA

(71) Applicant: Mitsubishi Chemical Corporation, Tokyo (JP)

(72) Inventors: Eiji Sato, Kanagawa (JP); Fujio Yu, Kanagawa (JP); Eiji Nakajima, Kanagawa (JP); Michiko Yamazaki, Kanagawa (JP); Wataru Mizunashi, Kanagawa (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 14/905,155

(22) PCT Filed: Jul. 25, 2014

(86) PCT No.: PCT/JP2014/003934
§ 371 (c)(1),
(2) Date: Jan. 14, 2016

(87) PCT Pub. No.: WO2015/015784
PCT Pub. Date: Feb. 5, 2015

(65) Prior Publication Data
US 2016/0145665 A1    May 26, 2016

(30) Foreign Application Priority Data

Aug. 1, 2013 (JP) .................... 2013-160302

(51) Int. Cl.
  C12P 19/32   (2006.01)
  C12P 7/52    (2006.01)
  C12N 9/88    (2006.01)

(52) U.S. Cl.
  CPC .............. *C12P 19/32* (2013.01); *C12N 9/88* (2013.01); *C12P 7/52* (2013.01)

(58) Field of Classification Search
  CPC ............... C12P 19/32; C12P 7/52; C12N 9/88
  USPC ...................................................... 435/272
  See application file for complete search history.

(56) References Cited

U.S. PATENT DOCUMENTS

| 2009/0275096 A1 | 11/2009 | Burgard et al. |
| 2011/0165640 A1 | 7/2011 | Mueller et al. |
| 2011/0201068 A1 | 8/2011 | Pharkya et al. |
| 2011/0252501 A1 | 10/2011 | Abad et al. |
| 2013/0065279 A1 | 3/2013 | Burk et al. |
| 2015/0184207 A1 | 7/2015 | Sato et al. |
| 2015/0191756 A1 | 7/2015 | Sato et al. |

FOREIGN PATENT DOCUMENTS

| EP | 2 848 694 A1 | 3/2015 |
| EP | 2 894 224 A1 | 7/2015 |
| JP | 2011-519561 A | 7/2011 |
| JP | 2013-504326 A | 2/2013 |
| WO | 2007/110394 A2 | 10/2007 |
| WO | 2 688 292 A1 | 12/2008 |
| WO | 2008/145737 A1 | 12/2008 |
| WO | 2009/135074 A2 | 11/2009 |
| WO | 2011/031897 A1 | 3/2011 |
| WO | 2012/135789 A2 | 10/2012 |
| WO | 2014/038214 A1 | 3/2014 |
| WO | 2014/038216 A1 | 3/2014 |

OTHER PUBLICATIONS

Uniprot Sequence C1A224_RHOE4, downloaded from http://www.uniprot.org/C1A224.txt on Mar. 28, 2018. (Year: 2018).*
Partial Supplementary European Search Report dated Jun. 28, 2016 in Patent Application No. 14832931.1.
"SubName: Full=Probable enoyl-CoA hydratase; EC=4.2.1.17" Database UniProt, Database Accession No. C1A224, XP002758833, May 26, 2009, 1 Page.
Sang-Hyun Pyo, et al., "A new route for the synthesis of methacrylic acid from 2-methyl-1,3-propanediol by integrating biotransformation and catalytic dehydration", Green Chemical, vol. 14, pp. 1942-1948, (Apr. 17, 2012).
G. J. Moskowitz, et al., "Metabolism of Poly-β-hydroxybutyrate. II. Enzymatic Synthesis of D-(−)-β-Hydroxybutyryl Coenzyme A by an Enoyl Hydrase from Rhodospirillum rubrum", Biochemistry, vol. 8, No. 7, pp. 2748-2755, (Jul. 1969).
Yoshiharu Shimomura, et al., "Purification and Partial Characterization of 3-Hydroxyisobutyryl-coenzyme A Hydrolase of Rat Liver", The Journal of Biological Chemistry, vol. 269, No. 19, pp. 14248-14253, (1994).
William G. Robinson, et al., "Coenzyme A Thiol Esters of Isobutyric, Methacrylic, and β-Hydroxyisobutyric Acids as Intermediates in the Enzymatic Degradation of Valine", J Biol Chem, vol. 224, pp. 1-11, (1957).

(Continued)

Primary Examiner — Paul C Martin
(74) Attorney, Agent, or Firm — Oblon, McClelland, Maier & Neustadt, L.L.P.

(57) ABSTRACT

The invention provides a method for producing methacrylyl-CoA that converts 3-hydroxyisobutyryl-CoA into methacrylyl-CoA using an enzyme having dehydratase activity as a method for producing methacrylyl-CoA using an enzyme catalyst. In this production method, conversion rate of 3-hydroxyisobutyryl-CoA into methacrylyl-CoA by the enzyme having dehydratase activity is 50% or higher. In this production method, furthermore, the enzyme having dehydratase activity derives from a microorganism belonging to the genus *Pseudomonas* or *Rhodococcus*.

10 Claims, No Drawings
Specification includes a Sequence Listing.

(56) References Cited

OTHER PUBLICATIONS

Mitsuo Sekine, et al., "Sequence analysis of three plasmids harboured in Rhodococcus erythropolis strain PR4", Enviromental Microbiology, vol. 8, No. 2, pp. 334-346, (2006).
International Search Report dated Oct. 21, 2014 in PCT/JP14/003934 Filed Jul. 25, 2014.

* cited by examiner

SEQUENCE LISTING

<160> NUMBER OF SEQ ID NOS: 8

<210> SEQ ID NO 1
<211> LENGTH: 258
<212> TYPE: PRT
<213> ORGANISM: Rhodococcus erythropolis PR4

<400> SEQUENCE: 1

```
Met Thr Asp Phe Asn Thr Ile Ile Leu Glu Arg Lys Gly Arg Val Gly
 1               5                  10                  15

Val Ile Thr Leu Asn Arg Pro Lys Ala Leu Asn Ala Leu Asn Ser Glu
            20                  25                  30

Leu Met Asn Glu Val Val Ala Val Ala Asp Leu Glu Ala Asp Asn
        35                  40                  45

Gly Ile Gly Ala Ile Leu Ile Thr Gly Ser Glu Arg Ala Phe Ala Ala
50                  55                  60

Gly Ala Asp Ile Lys Glu Met Gln Ser Lys Thr Tyr Met Asp Ala Tyr
65                  70                  75                  80

Val Glu Asp Phe Phe Thr Pro Trp Asp Arg Val Ala Ala Arg Lys
                85                  90                  95

Pro Leu Ile Ala Ala Val Ser Gly Tyr Ala Leu Gly Gly Gly Cys Glu
            100                 105                 110

Leu Ala Met Leu Cys Asp Phe Ile Ile Ala Ser Asp Thr Ala Lys Phe
        115                 120                 125

Gly Gln Pro Glu Ile Lys Leu Gly Val Ile Pro Gly Ile Gly Gly Ser
    130                 135                 140

Gln Arg Leu Thr Arg Ala Val Gly Lys Ala Lys Ala Met Glu Leu Cys
145                 150                 155                 160

Leu Thr Gly Arg Asn Met Asp Ala Glu Glu Ala Glu Arg Ala Gly Leu
                165                 170                 175

Val Ala Arg Ile Val Pro Ala Ala Asp Leu Leu Asp Asp Ala Leu Lys
            180                 185                 190

Thr Ala Thr Thr Ile Ala Glu Met Ser Leu Pro Ile Ala Met Met Ala
        195                 200                 205

Lys Glu Ala Val Asn Arg Ser Phe Glu Thr Thr Leu Ala Glu Gly Val
    210                 215                 220

Arg Phe Glu Arg Val Phe His Ser Thr Phe Ala Thr Glu Asp Gln
225                 230                 235                 240

Lys Glu Gly Met Thr Ala Phe Val Glu Lys Arg Ser Ala Glu Phe Lys
                245                 250                 255

His Arg
```

<210> SEQ ID NO 2
<211> LENGTH: 777
<212> TYPE: DNA
<213> ORGANISM: Rhodococcus erythropolis PR4

<400> SEQUENCE: 2

```
gtgaccgact tcaacaccat catcctcgag cgtaagggtc gcgtcggcgt catcacgctc    60
aaccgcccga aggctctcaa cgccctgaac tccgagctga tgaacgaggt cgtcgccgcg   120
gttgccgacc tcgaagcgga caacggcatc ggagccatcc tgatcaccgg ttccgagcgc   180
gccttcgccg ccggcgccga catcaaggaa atgcagtcca agacgtacat ggacgcatac   240
gtcgaagatt tcttcacccc gtgggaccgc gtcgcagccg ctcgtaagcc gctgatcgcc   300
gccgtctccg gtacgcgct cggtggtggc tgcgaactgg cgatgctctg cgatttcatc   360
atcgcttcgg ataccgcgaa gttcggccag cccgagatca agctcggtgt cattccgggt   420
atcggtggct cacagcgcct acgcgcgcc gtgggtaagg ccaaggccat ggagctgtgc   480
ctgaccggcc gcaacatgga cgcagaagag gccgagcgcg caggcctggt tgcccggatc   540
gttccggccg ccgatctgct cgacgacgca ttgaagaccg caaccaccat cgccgagatg   600
tcgctgccca tcgcgatgat ggccaaggaa gcggtcaacc gttccttcga gaccacactc   660
gccgagggcg tccgcttcga gcgtcgggtg ttccactcga ccttcgcgac ggaggatcag   720
aaggaaggca tgaccgcgtt cgtggagaag cggtccgccg agttcaagca ccgctga      777
```

<210> SEQ ID NO 3
<211> LENGTH: 272
<212> TYPE: PRT
<213> ORGANISM: Pseudomonas aeruginosa PA01

<400> SEQUENCE: 3

```
Met Asn Thr Ala Val Glu Pro Tyr Lys Ala Ser Ser Phe Asp Leu Thr
1               5                   10                  15

His Lys Leu Thr Val Glu Lys His Gly His Thr Ala Leu Ile Thr Ile
            20                  25                  30

Asn His Pro Pro Ala Asn Thr Trp Asp Arg Asp Ser Leu Ile Gly Leu
        35                  40                  45

Arg Gln Leu Ile Glu His Leu Asn Arg Asp Asp Ile Tyr Ala Leu
    50                  55                  60

Val Val Thr Gly Gln Gly Pro Lys Phe Phe Ser Ala Gly Ala Asp Leu
65                  70                  75                  80

Asn Met Phe Ala Asp Gly Asp Lys Ala Arg Ala Arg Glu Met Ala Arg
                85                  90                  95

Arg Phe Gly Glu Ala Phe Glu Ala Leu Arg Asp Phe Arg Gly Val Ser
            100                 105                 110

Ile Ala Ala Ile Asn Gly Tyr Ala Met Gly Gly Gly Leu Glu Cys Ala
        115                 120                 125

Leu Ala Cys Asp Ile Arg Ile Ala Glu Arg Gln Ala Gln Met Ala Leu
    130                 135                 140

Pro Glu Ala Ala Val Gly Leu Leu Pro Cys Ala Gly Gly Thr Gln Ala
145                 150                 155                 160

Leu Pro Trp Leu Val Gly Glu Gly Trp Ala Lys Arg Met Ile Leu Cys
                165                 170                 175

Asn Glu Arg Val Asp Ala Glu Thr Ala Leu Arg Ile Gly Leu Val Glu
            180                 185                 190

Gln Val Val Asp Ser Gly Glu Ala Arg Gly Ala Ala Leu Leu Leu Ala
        195                 200                 205

Ala Lys Val Ala Arg Gln Ser Pro Val Ala Ile Arg Thr Ile Lys Pro
    210                 215                 220

Leu Ile Gln Gly Ala Arg Glu Arg Ala Pro Asn Thr Trp Leu Pro Glu
225                 230                 235                 240
```

Glu Arg Glu Arg Phe Val Asp Leu Phe Asp Ala Gln Asp Thr Arg Glu
               245                 250                 255

Gly Val Asn Ala Phe Leu Glu Lys Arg Asp Pro Lys Trp Arg Asn Cys
        260                 265                 270

<210> SEQ ID NO 4
<211> LENGTH: 819
<212> TYPE: DNA
<213> ORGANISM: Pseudomonas aeruginosa PA01

<400> SEQUENCE: 4

| | | | | | |
|---|---|---|---|---|---|
| atgaacactg | ccgtcgaacc | ctacaaggct | tcctccttcg | acctgaccca | caagctcacc | 60 |
| gtggaaaagc | acgggcacac | cgcgctgatc | accatcaacc | cccgccggc | caacacctgg | 120 |
| gaccgcgact | cgctgatcgg | cctgcgccaa | ctgatcgagc | acctcaaccg | cgacgacgat | 180 |
| atctacgccc | tggtagtgac | cggccagggg | ccgaagttct | tctccgccgg | cgccgacctg | 240 |
| aacatgttcg | ccgacggcga | caaggcccgc | gctcgcgaga | tggcccgccg | cttcggcgaa | 300 |
| gccttcgagg | cgctgcgcga | tttccgcggg | gtgtcgatcg | cggcgatcaa | cggctacgcc | 360 |
| atgggcggcg | gcctggagtg | cgccctcgcc | tgcgacatcc | gcatcgccga | gcgccaggcg | 420 |
| cagatggccc | tgccggaggc | cgcggtgggc | ctgctgccct | gcgccggcgg | gacccaggcg | 480 |
| ctgccctggc | tggtgggcga | aggctgggcc | aagcggatga | tcctctgcaa | cgagcgggtg | 540 |
| gatgcggaaa | ccgccctgcg | catcggcctg | gtcgaacagg | tggtggacag | cggcgaggcg | 600 |
| cgcggcgccg | ccctgctgct | ggcggccaag | gtggcacgcc | agagcccggt | ggcgatccgc | 660 |
| accatcaagc | cgctgatcca | gggtgcccgc | gaacgcgcgc | cgaacacttg | gctgccggag | 720 |
| gagcgcgagc | gcttcgtcga | tctgttcgac | gcccaggaca | cccgcgaagg | ggtcaacgcc | 780 |
| ttcctcgaga | agcgcgatcc | caagtggcgc | aactgctga | | | 819 |

<210> SEQ ID NO 5
<211> LENGTH: 31
<212> TYPE: DNA
<213> ORGANISM: Artificial Sequence
<220> FEATURE:
<223> OTHER INFORMATION: MMA-031

<400> SEQUENCE: 5
ggtcatgacc gacttcaaca ccatcatcct c           31

<210> SEQ ID NO 6
<211> LENGTH: 34
<212> TYPE: DNA
<213> ORGANISM: Artificial Sequence
<220> FEATURE:
<223> OTHER INFORMATION: MMA-032

<400> SEQUENCE: 6
ggcctgcagg ttcagctgtt cgaaagttca gcgc        34

<210> SEQ ID NO 7
<211> LENGTH: 31
<212> TYPE: DNA
<213> ORGANISM: Artificial Sequence
<220> FEATURE:
<223> OTHER INFORMATION: MMA-025

<400> SEQUENCE: 7
ggtcatgaac actgccgtcg aaccctacaa g           31

```
<210> SEQ ID NO 8
<211> LENGTH: 35
<212> TYPE: DNA
<213> ORGANISM: Artificial Sequence
<220> FEATURE:
<223> OTHER INFORMATION: MMA-026

<400> SEQUENCE: 8
ggcctgcagg ctcagcagtt gcgccacttg ggatc                              35
```

METHOD FOR PRODUCING METHACRYLYL-COA

FIELD OF THE INVENTION

The present invention relates to a method for producing methacrylyl-CoA using an enzyme catalyst.

BACKGROUND ART

Methacrylic acid esters are used mostly as raw material for producing acrylic resins, but are also required as comonomers to be used in a variety of applications such as coatings, adhesives and resin modifiers. Examples of methods for industrially producing methacrylic acid esters are acetone cyanohydrin (ACH) methods that use acetone and hydrogen cyanide as raw materials, direct oxidation methods that use isobutylene and t-butyl alcohol as raw materials, and the like. Those chemical methods depend on fossil-based raw materials and require much energy.

From the viewpoints of global warming prevention and environmental protection, in recent years industries have focused on technologies for producing various chemical products using biomass as the carbon source so as to replace conventionally used fossil materials. Methacrylic acids and methacrylate esters are also expected to be produced from biomass material.

For example, methods are proposed for producing 2-hydroxyisobutyric acid and 3-hydroxyisobutyric acid to be used as precursors of methacrylic acids from natural products such as sugars by using naturally available microorganisms (see Patent Publications 1 and 2 and Non-patent Publication 1). Other proposed methods are for producing methacrylic acids from glucose using recombinant microorganisms that do not exist naturally but are constructed by introducing enzyme genes. However, those methods are based on combined enzymatic reactions of known reactions and what is assumed from those known reactions, and thus such reactions are not verified (see Patent Publications 3~5). Those publications provide descriptions showing that certain enzymes for catalyzing similar catalytic reactions may also be used for enzymatic dehydration reactions of 3-hydroxyisobutyric acid or 3-hydroxyisobutyryl-CoA. In fact, enoyl-CoA hydratase catalyzes dehydration reactions in the acetone/butanol fermentation pathway. So, if such certain enzymes take the above compounds as their specific substrates, they are thought to be effective. On the other hand, enoyl-CoA hydratase in β-oxidation of fatty acids or the degradation pathway of branched-chain amino acids is an enzyme for catalyzing hydration reactions but not for catalyzing dehydration reactions.

Non-patent Publication 2 has a description showing that enoyl-CoA hydratase purified from bacteria which produce poly-3-hydroxybutyrate has activities to catalyze dehydration reactions and reverse reactions (hydration reactions) of 3-hydroxybutyl-CoA. However, it is unknown whether other enoyl-CoA hydratases catalyze such two-way reactions. Moreover, there is no report in the above prior art as to whether methacrylyl-CoA has been synthesized by methods using 3-hydroxyisobutyryl-CoA as raw material. Considering diversity of enzymes and their substrate specificity, it is still unknown whether an enzyme for catalyzing only similar reactions is capable of producing methacrylyl-CoA having a structure different from its original substrate.

Meanwhile, methacrylyl-CoA is known as an intermediate in the metabolism of valine. Also, it is known to be cytotoxic. In living organisms, methacrylyl-CoA is promptly hydrated by the activity of enoyl-CoA hydratase, and is thought to be metabolized to 3-hydroxyisobutyrate through an intermediate stage of 3-hydroxyisobutyryl-CoA.

Non-patent Publication 3 describes examples in which crotonase is used to catalyze hydration reactions from methacrylyl-CoA to 3-hydroxyisobutyryl-CoA. The publication describes that the conversion rate in such reactions is lower than in other reactions (acrylyl-CoA→hydroxy propionyl-CoA) and that the reactions have reached equilibrium. However, such reactions are hydration reactions using methacrylyl-CoA as raw material, and it is totally unknown whether dehydration reactions actually progress using 3-hydroxyisobutyryl-CoA as raw material. Moreover, Non-patent Publication 4 describes spontaneous hydration reactions of methacrylyl-CoA. However, it is totally unknown whether, under aquatic conditions where methacrylyl-CoA is spontaneously hydrated, 3-hydroxyisobutyryl-CoA is actually dehydrated to produce methacrylyl-CoA as the product of interest in the present invention.

PRIOR ART PUBLICATION

Patent Publication

Patent Publication 1: WO2007/110394
Patent Publication 2: WO2008/145737
Patent Publication 3: WO2009/135074
Patent Publication 4: WO2011/031897
Patent Publication 5: WO2012/135789

Non-Patent Publication

Non-patent Publication 1: Green Chemistry, 2012, 14, 1942-1948
Non-patent Publication 2: Biochemistry, 1969, 8, 2748-2755
Non-patent Publication 3: Journal of Biological Chemistry, 1994, 269, 14248-14253
Non-patent Publication 4: Journal of Biological Chemistry, 1957, 224, 1-11

SUMMARY OF THE INVENTION

Problems to be Solved by the Invention

The objective of the present invention is to provide a method for producing methacrylyl-CoA using enzyme catalysts.

Solutions to the Problems

The inventors of the present invention have found that methacrylyl-CoA is synthesized from 3-hydroxyisobutyryl-CoA using an enzyme possessing dehydratase activity and have completed the present invention. Namely, the present invention is described as follows.

(1) A method for producing methacrylyl-CoA by converting 3-hydroxyisobutyryl-CoA to methacrylyl-CoA in the presence of a dehydratase.

(2) The production method described in (1), in which a hydratase with a conversion rate of 50% or higher is used for converting 3-hydroxyisobutyryl-CoA to methacrylyl-CoA.

(3) The production method described in (1) or (2), in which 3-hydroxyisobutyryl-CoA is converted to methacrylyl-CoA under reaction conditions of pH 4~10.

(4) The production method described in any of (1)~(3), in which 3-hydroxyisobutyryl-CoA is converted to methacrylyl-CoA under reaction conditions of temperature at 5~80° C.
(5) The production method described in any of (1)~(4), in which 3-hydroxyisobutyryl-CoA is converted to methacrylyl-CoA under reaction conditions of duration of 1 minute to 1 week.
(6) The production method described in any of (1)~(5), in which 3-hydroxyisobutyryl-CoA is prepared in an aqueous medium containing 1 mM or greater of an osmolyte.
(7) The production method described in any of (1)~(6), in which 3-hydroxyisobutyryl-CoA is converted to methacrylyl-CoA in the presence of a transformant for expressing the gene for encoding a dehydratase.
(8) The production method described in (7), in which the gene encoding a dehydratase is derived from a microorganism.
(9) The production method described in (8), in which the microorganism belongs to the genus *Pseudomonas* or the genus *Rhodococcus*.
(10) The production method described in (7) in which a dehydratase is selected from a group consisting of (a)~(f) below:
 (a) a protein having the amino acid sequence shown in SEQ ID NO: 1 or 3;
 (b) a protein having an amino acid sequence in which one or more amino acids are deleted from, substituted with, added to and/or inserted into the amino acid sequence shown in SEQ ID NO: 1 or 3, and possessing dehydratase activity;
 (c) a protein being at least 90% identical to a protein having the amino acid sequence shown in SEQ ID NO: 1 or 3, and possessing dehydratase activity;
 (d) a protein encoded by DNA having the base sequence shown in SEQ ID NO: 2 or 4;
 (e) a protein encoded by DNA that hybridizes with a DNA strand having the base sequence shown in SEQ ID NO: 2 or 4 under stringent conditions, and possessing dehydratase activity; and
 (f) a protein encoded by DNA that is at least 90% identical to a DNA strand having the base sequence shown in SEQ ID NO: 2 or 4, and possessing dehydratase activity.
(11) A method for producing methacrylyl-CoA by converting 3-hydroxyisobutyryl-CoA to methacrylyl-CoA in the presence of a transformant for expressing the gene encoding a dehydratase derived from a microorganism at a conversion rate of 50% or higher through reactions of a 3-hydroxyisobutyryl-CoA solution, which is prepared in an aqueous medium containing 1 mM or greater of an osmolyte, under reaction conditions of a pH at 4~10, a temperature at 5~80° C. and a duration of 1 minute to 1 week.

Effects of the Invention

According to the present invention, methacrylyl-CoA is produced by using enzyme catalysts. By combining the production method related to the present invention and metabolism in vivo or the like, fermentative production of methacrylic acids and their esters is also achieved. As a result, compared with conventional chemical production procedures, energy, resources and environmental load are significantly reduced, while methacrylic acid esters are efficiently produced.

DETAILED DESCRIPTION OF THE EMBODIMENTS

In the following, the present invention is described in detail.

In the embodiments of the present invention, methacrylyl-CoA is a compound represented by formula (1) below, and is known as an intermediate in the valine metabolism in vivo.

[chemical formula 1]

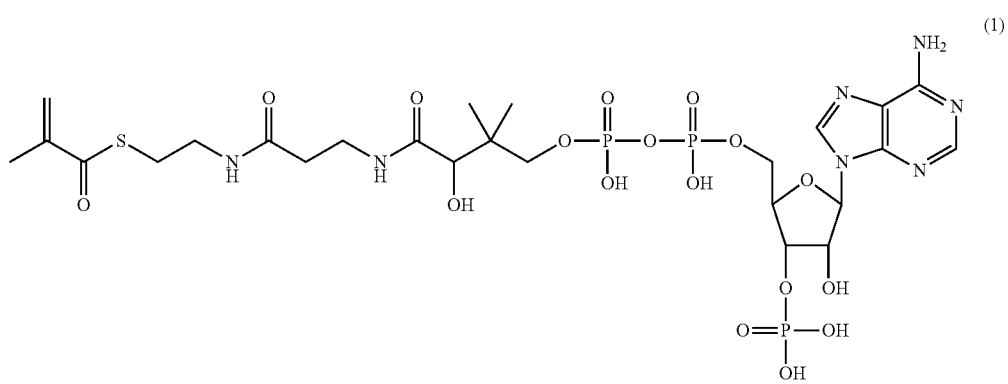

As a raw material for producing methacrylyl-CoA in the present invention, 3-hydroxyisobutyryl-CoA is a compound represented by formula (2) below, and is known as an intermediate in the valine metabolism in vivo.

[chemical formula 2]

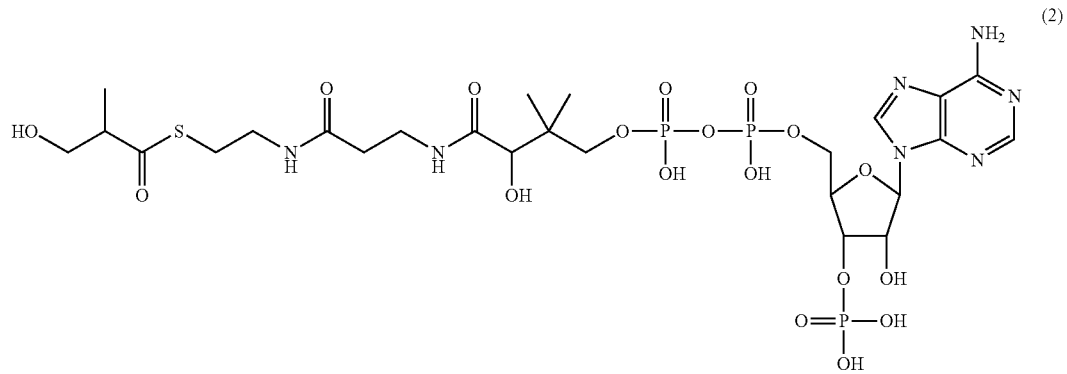

In the embodiments of the present invention, 3-hydroxyisobutyryl-CoA produced by a known or novel method is used. As for synthetic production methods, organic chemical synthesis (Angew. Chem. 1953, 65, 186-187) and synthesis using enzymatic reactions are known. Moreover, 3-hydroxyisobutyryl-CoA synthesized by metabolic engineering (fermentation) from biomass may also be used.

In the embodiments of the present invention, dehydratase activity indicates such activity that catalyzes reactions to remove a water molecule from the substrate molecule, especially such activity that catalyzes reactions to remove a water molecule from 3-hydroxyisobutyryl-CoA so as to produce methacrylyl-CoA. Specific examples of enzymes possessing dehydratase activity are those classified as enoyl-CoA hydratase (EC 4.2.1.17) or crotonase. Those enzymes take part in β-oxidation of fatty acids, acetone/butanol fermentation, and branched-chain amino acid metabolism.

Enzymes possessing dehydratase activity (hereinafter may be referred to as simply "dehydratase") for use in the embodiments of the present invention are not limited specifically as long as they are capable of converting 3-hydroxyisobutyryl-CoA to methacrylyl-CoA. Types or origins of such enzymes are not limited specifically. However, catalysts derived from living organisms are preferred, more preferably microorganism-derived dehydratases capable of catalyzing β-oxidation of fatty acids, acetone/butanol fermentation, and branched-chain amino acid degradation.

To select microorganism-derived dehydratases that are effective for use in the embodiments of the present invention, complete genome sequencing of such microorganisms may be used. From the complete genome sequencing, the inventors of the present invention have obtained sequence information of a gene that encodes the protein having dehydratase activity. Such information, or generally available sequence information of a gene that encodes the protein of enoyl-CoA hydratase or crotonase, is used to find highly homologous gene sequencing through homology search so that enzymes suitable for use in the embodiments of the present invention can be selected by the method described below. When the complete genome sequencing of a microorganism is unknown, the complete genome sequencing is first determined and a suitable enzyme is selected in the same manner. Here, because of widely available next-generation sequencers, it is easy for those skilled in the art to analyze complete genome sequencing.

Dehydratases used in the embodiments of the present invention are selected by checking catalytic activity as follows: the gene of an enzyme derived from a living organism and assumed to have dehydratase activity is isolated or totally synthesized by a known method; the gene is introduced to a generally available host vector system; a candidate protein is expressed by a microorganism transformed by the vector system: the protein is added in a solution containing 3-hydroxyisobutyryl-CoA, which is then put under reactions at 30° C.; after that, using liquid chromatography, whether or not methacrylyl-CoA is produced is verified.

In the present invention, preferred origins of enzymes are microorganisms that belong to the genus *Pseudomonas* or the genus *Rhodococcus*.

Specific examples of microorganism classified in the genus *Pseudomonas* are *Pseudomonas aeruginosa*, *Pseudomonas agarici*, *Pseudomonas alcaligenes*, *Pseudomonas amygdale*, *Pseudomonas anguiliseptica*, *Pseudomonas antimicrobica*, *Pseudomonas aspleni*, *Pseudomonas aurantiaca*, *Pseudomonas aureofaciens*, *Pseudomonas avellanae*, *Pseudomonas azotoformans*, *Pseudomonas balearica*, *Pseudomonas beijerinsckii*, *Pseudomonas beteli*, *Pseudomonas boreopolis*, *Pseudomonas carboxyhydrogena*, *Pseudomonas caricapapayae*, *Pseudomonas cichorii*, *Pseudomonas cissicola*, *Pseudomonas citronellolis*, *Pseudomonas coronafaci ens*, *Pseudomonas corrugate*, *Pseudomonas doudoroffii*, *Pseudomonas echinoids*, *Pseudomonas elongate*, *Pseudomonas ficuserectae*, *Pseudomonas flavescens*, *Pseudomonas flectens*, *Pseudomonas fluorescens*, *Pseudomonas fragi*, *Pseudomonas fulva*, *Pseudomonas fuscovaginae*, *Pseudomonas gelidicola*, *Pseudomonas geniculata*, *Pseudomonas glathei*, *Pseudomonas halophila*, *Pseudomonas hibiscicola*, *Pseudomonas huttiensis*, *Pseudomonas iners*, *Pseudomonas lancelota*, *Pseudomonas lemoignei*, *Pseudomonas lundensis*, *Pseudomonas luteola*, *Pseudomonas marginalis*, *Pseudomonas meliae*, *Pseudomonas mendocina*, *Pseudomonas mucidolens*, *Pseudomonas monteilli*, *Pseudomonas nautica*, *Pseudomonas nitroreducens*, *Pseudomonas oleovorans*, *Pseudomonas oryzihabitans*, *Pseudomonas pertucinogena*, *Pseudomonas phenazinium*, *Pseudomonas pictorum*, *Pseudomonas pseudoalcaligenes*, *Pseudomonas putida*, *Pseudomonas pyrrocinia*, *Pseudomonas resinovorans*, *Pseudomonas rhodesiae*, *Pseudomonas saccharo-* phila, *Pseudomonas savastanoi, Pseudomonas spinosa, Pseudomonas stanieri, Pseudomonas straminae, Pseudomonas stutzeri, Pseudomonas synxantha, Pseudomonas syringae, Pseudomonas syzygii, Pseudomonas taetrolens, Pseudomonas tolaasii, Pseudomonas veronii, Pseudomonas viridiflava, Pseudomonas vulgaris, Pseudomonas wisconsinensis*, and so on.

Specific examples of microorganism classified in the genus *Rhodococcus* are *Rhodococcus rhodocrous, Rhodococcus erythropolis, Rhodococcus equi, Rhodococcus opacus, Rhodococcus jostii, Rhodococcus pyridinovorans, Rhodococcus rhodnii, Rhodococcus corallinus, Rhodococcus rubropertinctus, Rhodococcus coprophilus, Rhodococcus globerulus, Rhodococcus chlorophenolicus, Rhodococcus luteus, Rhodococcus aichiensis, Rhodococcus chubuensis, Rhodococcus maris, Rhodococcus fascines*, and so on.

Dehydratases derived from the microorganisms listed above are preferred. Especially preferred are enzymes having a conversion rate of 50% or higher when converting methacrylyl-CoA from 3-hydroxyisobutyryl-CoA. The conversion rate is more preferred to be 55% or higher, even more preferably 60% or higher.

Here, a conversion rate of 50% or higher indicates that at least half the 3-hydroxyisobutyryl-CoA as raw material is converted to methacrylyl-CoA. Namely, it indicates that the produced amount of methacrylyl-CoA at the completion of reactions exceeds the remaining amount of 3-hydroxyisobutyryl-CoA used as raw material.

The conversion rate used in the embodiments of the present invention is obtained by the formula below.

[produced amount of methacrylyl-CoA]/[remaining amount of 3-hydroxyisobutyryl-CoA+produced amount of methacrylyl-CoA]×100

In the embodiments of the present invention, especially effective dehydratases are proteins selected from a group consisting of (a)~(f) below:

(a) a protein having the amino acid sequence shown in SEQ ID NO: 1 or 3;

(b) a protein having an amino acid sequence in which one or more amino acids are deleted from, substituted with, added to and/or inserted into the amino acid sequence shown in SEQ ID NO: 1 or 3, and possessing dehydratase activity;

(c) a protein being at least 90% identical to a protein having the amino acid sequence shown in SEQ ID NO: 1 or 3, and possessing dehydratase activity;

(d) a protein encoded by DNA having the base sequence shown in SEQ ID NO: 2 or 4;

(e) a protein encoded by DNA that hybridizes with a DNA strand having the base sequence shown in SEQ ID NO: 2 or 4 under stringent conditions, and possessing dehydratase activity; and (f) a protein encoded by DNA that is at least 90% identical to a DNA strand having the base sequence shown in SEQ ID NO: 2 or 4, and possessing dehydratase activity.

In the embodiments of the present invention, a dehydratase has the amino acid sequence shown as SEQ ID NO: 1 or 3.

In the present invention, a dehydratase is not limited to having the above sequence, but includes a protein having an amino acid sequence that is homologous or identical to the amino acid sequence in SEQ ID NO: 1 or 3 at approximately 50% or higher, preferably at approximately 60% or higher, more preferably at approximately 70% or higher, even more preferably at approximately 80% or higher, especially preferably at approximately 90% or higher, even more especially preferably at approximately 95% or higher, and most preferably at approximately 98% or higher, while also possessing dehydratase activity.

The percentage of sequence homology is determined by carrying out the maximum matching command, for example, using a sequencing analysis software DNASIS (made by Hitachi Software Engineering Co., Ltd.). The parameters are set as default (initial setting). Furthermore, a dehydratase related to the present invention includes a protein having an amino acid sequence in which one or more amino acids are deleted from, substituted with, added to and/or inserted into the amino acid sequence shown in SEQ ID NO: 1 or 3, and possessing dehydratase activity.

Amino acid sequences effective in the present invention are (i) an amino acid sequence in which 1~20 (for example, 1~10, preferably 1~5, more preferably 1~2) amino acids are deleted from the amino acid sequence shown in SEQ ID NO: 1 or 3;

(ii) an amino acid sequence in which 1~20 (for example, 1~10, preferably 1~5, more preferably 1~2) amino acids in the amino acid sequence shown in SEQ ID NO: 1 or 3 are substituted with other amino acids;

(iii) an amino acid sequence in which 1~20 (for example, 1~10, preferably 1~5, more preferably 1~2) amino acids are added to the amino acid sequence shown in SEQ ID NO: 1 or 3;

(iv) an amino acid sequence in which 1~20 (for example, 1~10, preferably 1~5, more preferably 1~2) amino acids are inserted into the amino acid sequence shown in SEQ ID NO: 1 or 3; and (v) an amino acid sequence obtained by combining (i)~(iv) above.

When one or more amino acids of the amino acid sequence are substituted, conservative substitution between similar amino acid residues is preferred. For example, based on the properties of their side chains, amino acids are classified as follows: hydrophobic amino acids (A, I, L, M, F, P, W, Y, V); hydrophilic amino acids (R, D, N, C, E, Q, G, H, K, S, T); amino acids with aliphatic side chains (G, A, V, L, I, P); amino acids with hydroxyl-group-containing side chains (S, T, Y); amino acids with sulfur-atom-containing side chains (C, M); amino acids with carboxylic-acid- and amide-containing side chains (D, N, E, Q); amino acids with base-containing side chains (R, K, H); and amino acids with aromatic side chains (H, F, Y, W). Those amino acids classified in the same group are known to maintain their polypeptide activity when substituted among themselves. Thus, substitution is preferred to be conducted among amino acids in the same group. Preferred examples of substitution are between glycine and proline, glycine and alanine or valine, leucine and isoleucine, glutamic acid and glutamine, aspartic acid and asparagine, cysteine and threonine, threonine and serine or alanine, and lysine and arginine.

In the embodiments of the present invention, the gene encoding a dehydratase includes DNA having the base sequence shown in SEQ ID NO: 2 or 4.

In the present invention, the gene that encodes a dehydratase is not limited to having the above sequence, but includes DNA having such a base sequence that is homologous (identical) to the base sequence in SEQ ID No: 2 or 4 at approximately 50% or higher, preferably at approximately 60% or higher, more preferably at approximately 70% or higher, even more preferably at approximately 80% or higher, especially preferably at approximately 90% or higher, even more especially preferably at approximately 95% or higher, and most preferably at approximately 98% or higher, as long as the DNA encodes a protein having dehydratase activity.

In addition, in response to the above amino acid sequence described as deleted, substituted, added and/or inserted, even if mutation such as deletion, substitution, addition and/or insertion has occurred in several bases of the base sequence shown in SEQ ID NO: 2 or 4, such a gene is included as that encoding a dehydratase as long as the gene encodes a protein having dehydratase activity. The number of bases deleted from, substituted with, added to and/or inserted into the base sequence is preferred to be 30 or less, more preferably 15 or less, especially preferably 6 or less.

Moreover, if DNA is capable of hybridizing under stringent conditions with a DNA strand having a base sequence complementary to the base sequence shown in SEQ ID NO: 2 or 4, the DNA is also included as the gene encoding a dehydratase as long as it encodes a protein having dehydratase activity.

In the present application, stringent conditions are, for example, conditions for cleaning after hybridization such as "2×SSC, 0.1% SDS, 42° C." or "1×SSC, 0.1% SDS, 37° C." More stringent conditions are, for example, "1×SSC, 0.1% SDS, 65° C.," "0.5×SSC, 0.1% SDS, 50° C." and the like.

Hybridization may be carried out using a known method. Hybridization methods are, for example, "Molecular Cloning, A Laboratory Manual 2nd ed." (Cold Spring Harbor Laboratory Press (1989)), "Current Protocols in Molecular Biology" (John Wiley & Sons (1987-1997)) and the like.

The aforementioned gene that encodes a dehydratase related to the present invention is introduced into a host to construct a transformant. For example, a transformant is obtained by forming one or more expression vectors containing the gene in such a way to be operatively linked to an expression control sequence that is functional in a host. In the embodiments of the present invention, expression vectors include plasmid vectors, phage (virus) vectors, cosmids, artificial chromosome vectors and the like. Expression vectors may include one or more selectable marker genes and proper expression control sequences. Many host-vector systems are known, but new vectors may be developed if necessary using the same method as above.

For example, a vector for expressing a dehydratase may be constructed by designing a primer for amplifying the gene encoding a dehydratase from the genome sequencing of *Pseudomonas aeruginosa* PA01, amplifying the gene through PCR using the genomic DNA as a template, and then incorporating the amplified gene into an expression vector for *E. coli*. Then, an expression plasmid containing the vector is constructed, which is then introduced to a host such as *E. coli* to form a recombinant (transformant). A cell extract obtained by cultivating the recombinant is used to produce methacrylyl-CoA from 3-hydroxyisobutyryl-CoA.

Examples of a host to express a dehydratase are bacteria such as *E. coli, Rhodococcus* spp., *Pseudomonas* spp., *Corynebacterium* spp., *Bacillus* spp., *Streptococcus* spp., and *Streptomyces* spp.; yeasts such as *Saccharomyces* spp., *Candida* spp., *Schizosaccharomyces* spp., and *Pichia* spp.; filamentous fungi such as *Aspergillus* spp.; and so on. Among those, *E. coli* is preferred since it is easy to obtain and efficient.

Methacrylyl-CoA is produced by using a transformant with the introduced gene that encodes a dehydratase. More specifically, the gene encoding a dehydratase is introduced into a host to form a transformant so that the dehydratase is expressed.

In synthetic reactions of methacrylyl-CoA, 3-hydroxyisobutyryl-CoA is used as a substrate, to which a dehydratase is brought into contact under appropriate conditions for reactions so that methacrylyl-CoA is obtained. For example, dehydratases are contained in a broth obtained by cultivating a recombinant microorganism, or in cells or treated cells obtained by a cell collecting process such as centrifugal separation of cells from the broth. Examples of treated cells are those treated by acetone, toluene and the like, freeze-dried cells, homogenized cells, cell-free extracts obtained from homogenized cells, crude or refined enzymes extracted from those treated cells, and so on. Preferred methods for collecting proteins from cells obtained by cultivating a transformant are homogenizing, extracting, centrifugal separation and the like.

Also, as described above, reactions for synthesizing methacrylyl-CoA may be conducted by using a transformant with the introduced gene that encodes a dehydratase so that 3-hydroxyisobutyryl-CoA is converted to methacrylyl-CoA in the presence of the transformant. A transformant, into which a group of enzyme genes capable of synthesizing 3-hydroxyisobutyryl-CoA is introduced in addition to the gene encoding a dehydratase, may be formed, and methacrylyl-CoA is produced using a precursor of 3-hydroxyisobutyryl-CoA as raw material. By such a method, methacrylyl-CoA is efficiently produced through metabolic engineering (fermentation) of biomass or the like.

Methacrylyl-CoA is produced as follows. A dehydratase is brought into contact with a 3-hydroxyisobutyryl-CoA solution or suspension, and 3-hydroxyisobutyryl-CoA is reacted while conditions such as temperature are controlled. As a result of such reactions, 3-hydroxyisobutyryl-CoA is dehydrated and methacrylyl-CoA is produced.

A solution containing 3-hydroxyisobutyryl-CoA is usually prepared by using an aqueous medium such as a buffer. Here, to achieve smooth reactions, the osmolarity and/or ionic strength may be controlled by using an osmolyte or the like. As for an osmolyte (may also be used as a pH buffer), any water soluble substance may be used as long as it is added to set the osmotic pressure to be equal to or higher than that of the interior of a cell or the like. Examples are organic or inorganic salts or sugars, preferably salts. Metallic salts or inorganic salts are preferred; especially preferred are alkali metal salts or hydrochloride. Examples are alkali metal phosphates, salts of amino groups and hydrochloric acids such as amino acids and tris(hydroxymethyl)aminomethane, sodium chloride and potassium chloride. Examples of sugars are preferably monosaccharides or oligosaccharides, more preferably monosaccharides or disaccharides, for example, glucose, sucrose, mannitol and the like. The osmolyte is preferred to be added to have a 1 mM concentration or higher. Especially, the solution is preferred to be adjusted so as to be equal to or higher than that of the interior of a cell to be used. The concentration of the osmolyte in a solution containing 3-hydroxyisobutyryl-CoA is preferred to be 1 mM or higher, more preferably 50 mM or higher.

The concentration of 3-hydroxyisobutyryl-CoA in a reaction solution is not limited specifically. In addition, the amount of an enzyme having dehydratase activity and reaction conditions are appropriately determined according to the raw material to be used. Usually, the concentration of 3-hydroxyisobutyryl-CoA is set within a range of 0.00001~10 wt %, preferably within a range of 0.0001~1 wt %.

Other conditions such as reaction temperatures and reaction time are not limited specifically, and are appropriately determined depending on raw material, activity of the biocatalyst and the like. Usually, preferred conditions for reactions are 1 minute to 1 week at 5~80° C., more preferably at 10~70° C. for 1 minute to 120 hours, even more preferably for 10 minutes or longer. From such conditions, it is preferred to select those that allow reactions to be completed. The pH of the reaction solution is not limited specifically as long as reactions progress efficiently; for example, a range of pH 4~10, more preferably pH 5.5~8.5.

In the embodiments of the present invention, it is preferred to use a dehydratase with a conversion rate of 50% or higher from 3-hydroxyisobutyryl-CoA to methacrylyl-CoA, more preferably, with a conversion rate of 55% or higher, even more preferably 60% or higher. Reaction conditions are preferred to be set appropriate to the properties of a dehydratase.

In addition, to progress reactions efficiently, 3-hydroxyisobutyryl-CoA may be reacted in a system where an organic solvent is added in advance. Examples of organic solvents are straight-chain, branched or ring-type saturated or unsaturated aliphatic hydrocarbons or saturated or unsaturated aromatic hydrocarbons. They may be used alone or in combination thereof. Specific examples are hydrocarbon-based solvents (such as pentane, hexane, cyclohexane, benzene, toluene, and xylene), halogenated hydrocarbon solvents (such as methylene chloride, and chloroform), ether-based solvents (such as diethyl ether, dipropyl ether, diisopropyl ether, dibutyl ether, t-butyl methyl ether, and dimethoxyethane), ester-based solvents (such as methyl formate, methyl acetate, ethyl acetate, butyl acetate, and methyl propionate), and the like.

The methacrylyl-CoA produced by the method related to the present invention may be put through high-performance liquid chromatography (HPLC) for measurement or quantitative analysis. To isolate methacrylyl-CoA from the reaction solution, a known isolation method using a separation column may be employed.

Moreover, the obtained methacrylyl-CoA may be converted to methacrylic acid by chemically or enzymatically cutting thioester bonds, or may be converted to methacrylate ester by reacting the methacrylyl-CoA with alcohol. Namely, the method related to the present invention can include a process for producing methacrylic acid or methacrylate ester from methacrylyl-CoA.

By forming a transformant, into which a group of genes of an enzyme capable of synthesizing 3-hydroxyisobutyryl-CoA from biomass and the gene of an enzyme for catalyzing thioester bonding are all introduced in addition to the gene encoding a dehydratase, methacrylic acid or methacrylate ester may be directly synthesized through metabolic engineering (fermentation) of biomass.

Methacrylic acid or methacrylic acid ester obtained above is effective in remarkably reducing energy, resources and environmental load, and exhibits significantly high social values because it is an environmentally low-load material, compared with conventional chemical products manufactured using petroleum products as raw material.

In the following, the present invention is described in detail by referring to the examples. However, the present invention is not limited to the scope of those examples.

Example 1

Producing Recombinant *E. coli* Having Dehydratase Gene Derived from *Rhodococcus erythropolis* PR4 (NBRC 100887)

<Preparation of Genomic DNA from *Rhodococcus*>

*Rhodococcus erythropolis* PR4 (NBRC 100887) strain grown on an LB agar medium (1% bactorypton, 0.5% Bacto Yeast Extract, 0.5% NaCl, 1.5% agar) was inoculated into 10 mL of an LB liquid medium (1% bactorypton, 0.5% Bacto Yeast Extract, 0.5% NaCl), and underwent shaking culture at 30° C. for 36 hours. After the completion of shaking culture, 2 mL of cells were collected by centrifugation. Then, 100 μL of genomic DNA was obtained using a Wizard Genomic DNA Purification Kit (made by Promega Corp.)

<Construction of Dehydratase Expression Plasmid>

Using the genomic DNA as a template, a DNA fragment assumed to include the gene that encodes a dehydratase was prepared through PCR so as to be formed with a restriction enzyme recognition site that makes it easier to be inserted into an expression vector.

```
Oligonucleotide primer:
MMA-031:
                                    (SEQ ID NO: 5)
5'-GGTCATGACCGACTTCAACACCATCATCCTC-3'

MMA-032:
                                    (SEQ ID NO: 6)
5'-GGCCTGCAGGTTCAGCTGTTCGAAAGTTCAGCGC-3'
```

Composition of Reaction Solution:

| | |
|---|---|
| Sterile water | 22 μL |
| 2 × PrimeSTAR (made by Takara Bio, Inc.) | 25 μL |
| MMA-031 (SEQ ID NO: 5) | 1 μL |
| MMA-032 (SEQ ID NO: 6) | 1 μL |
| Genomic DNA | 1 μL |
| Total | 50 μL |
| Temperature cycle: | |
| 30 cycles of a reaction cycle: 98° C. for 10 seconds, 55° C. for 15 seconds, and 72° C. for 150 seconds | |

Approximately 0.8 kb of the amplified product band was purified using QIAquick® Gel Extraction Kit (made by QIAGEN). The purified DNA was cut by restriction enzymes BspHI (a cleavage recognition site is contained in oligonucleotide MMA-031) and Sse8387 I (a cleavage recognition site is contained in oligonucleotide MMA-032). Then, agarose gel electrophoresis was performed to separate the target band, which was then purified from the gel using Gel/PCR Purification Kit (made by Favorgen Biotech Corp.) and dissolved in 30 μL of sterile water. The purified DNA fragment (5 μL), vector pTrc 99A (1 μL) which was pre-digested with NcoI and Sse8387 I, distilled water (4 μL) and solution I (DNA Ligation Kit ver. 2 (Takara Bio, Inc.)) (10 μL) were mixed and cultivated at 16° C. for 12 hours. Accordingly, the PCR amplified product and the vector were ligated.

*E. coli* JM109 strain was inoculated into 1 mL of an LB medium and was precultivated at 37° C. for 5 hours in aerobic conditions. Then, 0.4 mL of the obtained culture was added to 40 mL of an SOB medium (2% Bacto Tryptone, 0.5% Bacto Yeast Extract, 10 mM NaCl, 2.5 mM KCl, 1 mM MgSO$_4$, 1 mM Mg Cl$_2$) and was cultivated at 18° C. for 20 hours. Cells were harvested from the culture through centrifugation, 13 mL of a cold TF solution (20 mM PIPES-KOH (pH 6.0), 200 mM KCl, 10 mM CaCl$_2$, 40 mM MnCl$_2$) was added to the cells, and the mixture was left standing at 0° C. for 10 minutes. Then, the mixture was centrifuged again to remove the supernatant. The precipitated *E. coli* cells were suspended in 3.2 mL of a cold TF solution, to which 0.22 mL of dimethyl sulfoxide was added, and then the mixture was left standing at 0° C. for 10 minutes.

To 200 µL of the prepared competent cells, 10 µL of the above ligated reactant solution was added and left standing at 0° C. for 30 minutes. Then, heat shock was applied to the mixture at 42° C. for 30 seconds, and the mixture was cooled at 0° C. for 2 minutes. After that, 1 mL of an SOC medium (20 mM glucose, 2% Bacto Tryptone, 0.5% Bacto Yeast Extract, 10 mM NaCl, 2.5 mM KCl, 1 mM MgSO$_4$, 1 mM MgCl$_2$) was added, and shaking culture was carried out at 37° C. for an hour.

After the completion of shaking culture, 100 µL each was applied on an LBAmp agar medium (LB medium containing 100 mg/L of ampicillin, and 1.5% agar) and cultivated at 37° C. Multiple transformant colonies grown on the agar medium were applied on 1.5 mL of an LBAmp medium (LB medium containing 100 mg/L of ampicillin) and cultivated at 37° C. overnight. Cells were collected and plasmid DNA was prepared using a QIAprep® Spin Miniprep Kit (QIAGEN).

The base sequence of the obtained recombinant plasmid DNA was confirmed using a CEQ DTCS Quick Start Kit and a fluorescent sequencer CEQ 2000XL DNA Analysis (both made by Beckman Coulter, USA), and was named plasmid pMMA 011. *E. coli* strain JM109 was transformed using plasmid pMMA 011 to produce a dehydratase expression recombinant.

Example 2

Synthesis of Methacrylyl-CoA from 3-Hydroxyisobutyryl-CoA Using Cell Extract of Recombinant *E. coli* for Expressing Gene that Encodes a Dehydratase Derived from *Rhodococcus erythropolis* PR4 (NBRC 100887)

1) Preparation of Cell Homogenate Having Dehydratase Activity

The recombinant *E. coli* JM109/pMMA011 obtained in Example 1 having the gene that encodes a dehydratase was inoculated into 2 mL of the LBAmp medium and cultivated at 37° C. for 24 hours. Then, 0.1 mL of the broth was added to 100 mL of a 1 mM IPTG medium, and shaking culture of the broth was carried out at 37° C. for 24 hours. After collected from the broth by centrifugation (3,700×g, 10 minutes, 4° C.), the cells were washed twice with a 10 mM sodium phosphate buffer (pH 7.0) and suspended in the buffer so as to set an OD630 nm value of 6.

From the cell suspension, 1 mL of a cell homogenate was prepared as follows: the cell suspension was homogenized for 5 minutes using an ultrasonic homogenizer VP-300 (Titec Co., Ltd., Japan) under ice-cooling conditions of 15% output power (amplitude)/On: 1 second and Off: 1 second.

2) Synthesis Reaction of Methacrylyl-CoA Using Cell Homogenate of Recombinant *E. coli* for Expressing Gene that Encodes Dehydratase Into 0.05 mL of a 1.0 M tris-HCl buffer (pH 7.4), 0.2 mL of 5 mM 3-hydroxyisobutyryl-CoA and 0.65 mL of water were mixed, and 0.1 mL of the above cell homogenate having enoyl-CoA hydratase activity was further added to obtain 1 mL of a reaction solution. The solution was reacted at 37° C. for 3 hours. The reaction product was analyzed under HPLC conditions below. As a result, 0.6 mM methacrylyl-CoA was confirmed to be produced. The remaining amount of 3-hydroxyisobutyryl-CoA was 0.33 mM. The conversion rate of methacrylyl-CoA from 3-hydroxyisobutyryl-CoA was 65% (=0.6/(0.33±0.6)×100).

(Conditions for HPLC Analysis)
Column: Capcell Pak ODS-UG120 (made by Shiseido Co., Ltd.), 2.0 mm×250 mm
Mobile phase: 25% MeOH, 50 mM H$_3$PO$_4$, pH 5.7
Flow rate: 1.0 mL/min.
Column temperature: 40° C.
Detection: UV 254 nm
Injection amount: 10 µL (reaction solution was diluted 10-fold with the mobile phase)

Example 3

Construction of Recombinant *E. coli* Introduced Gene that Encodes Dehydratase Derived from *Pseudomonas aeruginosa* PA01 (NBRC 106052)

<Preparation of Genomic DNA from *Pseudomonas*>
The same as in Example 1, genomic DNA was obtained from *Pseudomonas aeruginosa* PA01 strain cultivated on 10 mL of an LB liquid medium.

<Construction of Dehydratase Expression Plasmid>
Using the oligonucleotide primers below, and genomic DNA of *Pseudomonas aeruginosa* PA01 strain (NBRC 106052) as a template, a DNA fragment (approximately 0.8 kb) containing the gene assumed to encode a dehydratase was amplified the same as in Example 1.

```
Oligonucleotide primers:
MMA-025:
                                     (SEQ ID NO: 7)
5'-GGTCATGAACACTGCCGTCGAACCCTACAAG-3'

MMA-026:
                                     (SEQ ID NO: 8)
5'-GGCCTGCAGGCTCAGCAGTTGCGCCACTTGGGATC-3'
```

The DNA fragment was digested with BspHI and Sse8387 I, and was then incorporated into vector pTrc99A, the same as in Example 1. The resultant plasmid was named pMMA015. *E. coli* JM109 strain was transformed using plasmid pMMA015 to construct a dehydratase expression recombinant.

Example 4

Synthesis of Methacrylyl-CoA from 3-Hydroxyisobutyryl-CoA Using Cell Extract of Recombinant *E. coli* for Expressing Gene that Encodes a Dehydratase Derived from *Pseudomonas aeruginosa* PA01 (NBRC 106052)

1) Preparation of Cell Homogenate Having Dehydratase Activity

The recombinant *E. coli* JM109/pMMA015 obtained in Example 3 having the introduced dehydratase gene was cultivated and the cells were collected using the same methods described in 1) of Example 2. Accordingly, a cell suspension was obtained. Then, a cell homogenate was prepared from the cell suspension using the same method described in 1) of Example 2.

2) Synthesis Reaction of Methacrylyl-CoA Using Cell Homogenate of Recombinant *E. coli* for Expressing Gene that Encodes Dehydratase Into 0.05 mL of a 1.0 M tris-HCl buffer (pH 7.4), 0.2 mL of 5 mM 3-hydroxyisobutyryl-CoA and 0.65 mL of water were mixed, and 0.1 mL of the above cell homogenate having enoyl-CoA hydratase activity was further added to obtain 1 mL of a reaction solution. The solution was reacted at 37° C. for 3 hours. The reaction product was analyzed under HPLC conditions shown in 2) of Example 2. As a result, 0.6 mM methacrylyl-CoA was confirmed to be produced. The remaining amount of 3-hydroxyisobutyryl-CoA was 0.37 mM. The conversion rate of methacrylyl-CoA from 3-hydroxyisobutyryl-CoA was 62% (=0.6/(0.37±0.6)×100).

SEQ ID NO 5:
MMA-031

SEQ ID NO 6:
MMA-032

SEQ ID NO 7:
MMA-025

SEQ ID NO 8:
MMA-026

What is claimed is:

1. A method for producing methacrylyl-CoA and converting methylacryl-CoA to methacrylic acid or methacrylate ester, the method comprising:
converting 3-hydroxyisobutyryl-CoA to methacrylyl-CoA in an aqueous medium in the presence of a dehydratase at a conversion rate of 50% or higher; and
converting methacrylyl-CoA to methacrylic acid or methacrylate ester at a pH of 4 to 10,
wherein the dehydratase is selected from a group consisting of:
(a) a protein having the amino acid sequence shown in SEQ ID NO: 1 or 3;
(b) a protein that is at least 80% identical to a protein having the amino acid sequence shown in SEQ ID NO: 1 or 3, and possessing dehydratase activity;
(c) a protein encoded by the nucleotide sequence of SEQ ID NO: 2 or 4;
(d) a protein encoded by DNA that is at least 80% identical to SEQ ID NO: 2 or 4, and possessing dehydratase activity.

2. The method according to claim 1, wherein 3-hydroxyisobutyryl-CoA is converted to methacrylyl-CoA at a temperature of 5~80° C.

3. The method according to claim 1, wherein 3-hydroxyisobutyryl-CoA is converted to methacrylyl-CoA for a duration of from 1 minute to 1 week.

4. The method according to claim 1, wherein the aqueous medium comprises 1 mM or greater of an osmolyte.

5. The method according to claim 1, wherein 3-hydroxyisobutyryl-CoA is converted to methacrylyl-CoA in the presence of a transformant for expressing a gene for encoding a dehydratase.

6. The method according to claim 5, wherein the gene encoding a dehydratase is derived from a microorganism.

7. The method according to claim 6, wherein the microorganism belongs to the genus *Pseudomonas* or the genus *Rhodococcus*.

8. The method according to claim 1, wherein the dehydratase has the amino acid sequence shown in SEQ ID NO: 1 or 3.

9. A method for producing methacrylyl-CoA, the method comprising:
converting 3-hydroxyisobutyryl-CoA to methacrylyl-CoA in the presence of a transformant for expressing a gene encoding a dehydratase derived from a microorganism at a conversion rate of 50% or higher through reactions of a 3-hydroxyisobutyryl-CoA solution, which is prepared in an aqueous medium comprising 1 mM or greater of an osmolyte, at a pH of 4-10 and a temperature of 5-80° C. for a duration of from 1 minute to 1 week,
wherein the dehydratase is selected from a group consisting of:
(a) a protein having the amino acid sequence shown in SEQ ID NO: 1 or 3;
(b) a protein that is at least 80% identical to a protein having the amino acid sequence shown in SEQ ID NO: 1 or 3, and possessing dehydratase activity;
(c) a protein encoded by the nucleotide sequence of SEQ ID NO: 2 or 4;
(d) a protein encoded by DNA that is at least 80% identical to SEQ ID NO: 2 or 4, and possessing dehydratase activity.

10. The method according to claim 9, wherein the dehydratase has the amino acid sequence shown in SEQ ID NO: 1 or 3.

* * * * *